(12) United States Patent
Mawer et al.

(10) Patent No.: US 7,800,056 B2
(45) Date of Patent: Sep. 21, 2010

(54) DOCUMENT SAMPLER AND METHOD OF SAMPLING A DOCUMENT

(75) Inventors: Bill Mawer, Welwyn (GB); Geoff Beyer, Caledon (CA); Mark Elliot, Ontario (CA); Mark Piniarski, Mississauga (CA); Roland Link, Barrie (CA); Simon Feldberg, Thornhill (CA)

(73) Assignee: Smiths Detection Montreal Inc., Montreal (CA)

( * ) Notice: Subject to any disclaimer, the term of this patent is extended or adjusted under 35 U.S.C. 154(b) by 46 days.

(21) Appl. No.: 11/976,428

(22) Filed: Oct. 24, 2007

(65) Prior Publication Data

US 2008/0217524 A1    Sep. 11, 2008

Related U.S. Application Data

(60) Provisional application No. 60/863,007, filed on Oct. 26, 2006.

(51) Int. Cl.
*B01D 59/44* (2006.01)
*H01J 49/00* (2006.01)
*G01N 1/20* (2006.01)

(52) U.S. Cl. .................................. 250/288; 73/863.56
(58) Field of Classification Search ................ 250/281, 250/282, 288; 73/863.01, 863.56, 863.83, 73/864.65, 35.14–35.17
See application file for complete search history.

(56) References Cited

U.S. PATENT DOCUMENTS

| | | | | |
|---|---|---|---|---|
| 5,083,019 A | * | 1/1992 | Spangler | 250/287 |
| 5,585,575 A | * | 12/1996 | Corrigan et al. | 73/863.71 |
| 5,741,984 A | * | 4/1998 | Danylewych-May et al. | 73/864.71 |
| 6,334,365 B1 | * | 1/2002 | Linker et al. | 73/864.81 |
| 6,446,514 B1 | * | 9/2002 | Danylewych-May et al. | 73/863.21 |
| 6,613,571 B2 | * | 9/2003 | Cordery et al. | 73/863.51 |
| 6,633,032 B2 | * | 10/2003 | Houge et al. | 250/288 |
| 7,204,125 B2 | * | 4/2007 | Fine et al. | 73/864.81 |
| 2002/0124664 A1 | * | 9/2002 | Call et al. | 73/863.22 |
| 2005/0019220 A1 | * | 1/2005 | Napoli | 422/99 |
| 2005/0058575 A1 | * | 3/2005 | Ishikawa et al. | 422/83 |
| 2007/0089542 A1 | * | 4/2007 | Strohmeyer et al. | 73/864.31 |
| 2007/0169570 A1 | * | 7/2007 | Napoli | 73/864 |
| 2007/0295208 A1 | * | 12/2007 | Fairchild | 95/74 |
| 2008/0264186 A1 | * | 10/2008 | Nacson et al. | 73/863.12 |

* cited by examiner

*Primary Examiner*—Jack I Berman
*Assistant Examiner*—Brooke Purinton
(74) *Attorney, Agent, or Firm*—Foley & Lardner LLP (57) ABSTRACT

A document sampler can be arranged to receive a document in an insertion area of the document sampler. With such arrangements, a document can be directly inserted into a document sampler without an extra step of swabbing a document with a sample collection device. By eliminating the extra step of swabbing a document, the efficiency of sample detection is improved, sample detection is performed more rapidly, and operating costs of sample detection are decreased.

19 Claims, 10 Drawing Sheets

DOCUMENT SAMPLER AND METHOD OF SAMPLING A DOCUMENT

BACKGROUND

Trace analyte detection has numerous applications, such as screening individuals and baggage at transportation centers, mail screening, facility security applications, military applications, forensics applications, narcotics detection and identification, cleaning validation, quality control, and raw material identification. Trace analyte detection is the detection of small amounts of analytes, often at nanogram to picogram levels. Trace analyte detection can be particularly useful for security applications such as screening individuals or items for components in explosive materials, narcotics, chemical substances, or biological contaminants where small amounts of these components are deposited on the individual or on the surface of a package or bag.

A variety of different techniques can be used for trace analyte detection. These methods include ion mobility spectrometry (IMS), mass spectrometry, gas chromatography, liquid chromatography, and high performance liquid chromatography (HPLC).

IMS is a particularly useful technique for rapid and accurate detection and identification of trace analytes such as narcotics, explosives, and chemical warfare agents. The fundamental design and operation of an ion mobility spectrometer is addressed in, for example, Ion Mobility Spectrometry (G. Eiceman and Z. Karpas, 2d Ed., CRC Press, Boca Raton, Fla., 2004). IMS detects and identifies known analytes by detecting a signal which is unique for each analyte. IMS measures the drift time of ions through a fluid, such as clean, dry ambient air at atmospheric pressure. Analysis of analytes in a sample begins with collection of a sample and introduction of the sample into the spectrometer. A sample is heated to transform analyte from solid, liquid or vapor preconcentrated on a particle into a gaseous state. Analyte molecules are ionized in the reaction region of the IM spectrometer. Ions are then spatially separated in the IMS drift region in accordance to their ion mobility, which is an intrinsic property of an ion. Often, an induced current at the collector generates a signature for each ion as a function of the time required for that ion to reach the collector. This signature can be used to identify a specific analyte.

An advantage of using IMS for trace detection is the ability to analyze a sample in both positive and negative mode and using different ionization reagents to identify substances that cannot be differentiated by other methods. For example, ranitidine and cocaine have similar mobility constants in the positive mode. However, only ranitidine is ionized in the negative ion mode, allowing differentiation of ranitidine and cocaine when the positive and negative mode data both are collected and analyzed. Additionally, ammonium nitrate can be difficult to distinguish from other analytes containing ammonium ions or nitrate ions, but can be differentiated when the results from both positive and negative mode ionization are analyzed.

Trace detection can be useful for detecting analytes on documents. For example, travel documents, such as passports and visas, may contain analytes because a traveler has handled illicit or illegal substances before handling the travel documents. Conventional detection devices require an operator to collect a sample from a surface of a targeted document with a sample collection device, such as by swabbing or wiping the surface, and then inserting the sample collection device into a detection instrument for analysis. Such a procedure requires multiple steps, which slows the detection process.

SUMMARY

Thus, there is need in the art for a system that is efficient, easy to use, and rapidly detects analytes on documents.

According to an embodiment, a document sampler comprises an analytical device; and an insertion area formed by the document sampler, wherein the insertion area is configured so that a document can be inserted into the document sampler.

According to an embodiment, a method of acquiring and analyzing samples from documents comprises the steps of inserting a document into an insertion area of a document sampler; acquiring a sample from the document; and providing the sample to an analytical device for analysis.

It is to be understood that both the foregoing general description and the following detailed description are exemplary and explanatory only, and are not restrictive of the invention as claimed.

BRIEF DESCRIPTION OF THE DRAWINGS

These and other features, aspects, and advantages will become apparent from the following description, appended claims, and the accompanying exemplary embodiments shown in the drawings, which are briefly described below.

DETAILED DESCRIPTION

The inventors have discovered a document sampler and method of sampling a document that is efficient, easy to use, and rapidly detects samples on documents. According to embodiments described herein, a document sampler can be arranged to receive a document in an insertion area of the document sampler. With such arrangements, a document can be directly inserted into a document sampler without the extra step of swabbing or swiping a document with a sample collection device. By eliminating the extra step of swabbing or swiping a document, the efficiency of sample detection is improved, sample detection is performed more rapidly, and operating costs of sample detection are decreased. A document sampler can be used for security operations, such as sampling passenger passports as standard procedure at security or customs checkpoints, such as in airports prior to boarding or disembarking from an aircraft. By providing rapid, accurate analysis of passenger documents, a document sampler can be used to screen as much as 100% of the passengers through a security or customs checkpoint.

"Document" refers, without limitation, to any paper, blend of paper, polymer, plastic, textile, cloth, blend of cloth, or combination thereof that can attach, adsorb, absorb, imbed, or otherwise carry a sample. A "document" can be an object that is carried by a person, such as a passport, visa, travel document, driver's license, credit card, or other form of documentation or identification. A "document" can be a rigid or semi-rigid object.

"Sample" refers, without limitation, to any molecule, compound or complex that is adsorbed, absorbed, or imbedded on or within a document or sample collection device. A sample can contain an analyte of interest, referred to herein as an "analyte" or "sample analyte," which is understood to be any analyte to be detected using a detection technique. A "sample" can be a liquid, vapor, gas, particulate, solid, or any combination of these phases of matter. A "sample collection device" can include a swab, a manual sampling substrate, a sampling wand, or other sample collection device known in the art.

A wide range of analytes can be detected with a document sampler, including but not limited to explosives, narcotics, chemical warfare agents, toxins, pharmaceutical process contaminants, and other chemical compounds. Collected samples to be analyzed by a document sampler may be liquid, solid, vapors pre-concentrated on solid absorbents, or other appropriate sample collection forms.

Explosives that can be analyzed include, but are not limited to, 2-amino-4,6-dinitrotoluene, 4-amino-2,6-dinitrotoluene, ammonal, ammonium nitrate, black powder, 2,4-dimethyl-1,3-dinitrobutane, 2,4-dinitrotoluene, ethylene glycol dinitrate, forcite 40, GOMA-2, hexanitrostilbene, 1,3,5,7-tetranitro-1,3,5,7-tetrazacyclooctane (HMX), mononitrotoluene, nitroglycerine, pentaerythritol tetranitrate (PETN), 1,3,5-trinitro-1,3,5-triazacyclohexane (RDX), semtex-A, Semtex-H, smokeless powder, trinitro-2,4,6-phenylmethylnitramine tetryl (Tetryl), 2,4,6-trinitrotoluene (TNT), trilita, and 1,3,5-trinitrobenzene and combinations of these compounds. In one embodiment, the explosive which are collected are 1,3,5-trinitro-1,3,5-triazacyclohexane, pentaerythritol tetranitrate, 2,4,6-trinitrotoluene, tri nitro-2,4,6-phenylmethylnitramine tetryl, nitroglycerine, ammonium nitrate, 3,5,7-tetranitro-1,3,5,7-tetrazacyclooctane, and combinations thereof.

Narcotics that can be analyzed include, but are not limited to 6-acetylmorphine, alprazolam, amobarbital, amphetamine, antipyrine, benzocaine, benzoylecgonine, bromazepam, butalbital, carbetapentane, cathinone, chloradiazepoxide, chlorpheniramine, cocaethylene, cocaine, codeine, diazepam, ecgonine, ecognine methyl ester (EME), ephedrine, fentanyl, flunitrazepam, hashish, heroin, hydrocodone, hydromorphone, ketamine, lidocaine, lorazepam, lysergic acid diethylamide (LSD), lysergic acid, N-methyl-1-3(3,4-methylenedioxyohenyl)-2-butanamine (MBDB), 3,4-methylenedioxyamphetamine (MDA), DL-3,4-methylenedioxyethylamphetamine (MDEA), methylenedioxymethamphetamine (MDMA), marijuana, mescaline, methadone, methamphetamine, methaqualone, methcathinone, morphine, noscapine, opium, oxazepam, oxycodone, phencyclidine (PCP), pentobarbital, phenobarbital, procaine, psilocybin, secobarbital, temazepam, THC, THC—COOH, and triazolam. In one embodiment, the narcotics which can be collected with a sample collection device include cocaine, heroin, phencyclidine, TH C, methamphetamine, methylenedioxyethylamphetamine, methylenedioxymethamphetamine, N-methyl-1-3(3,4-methylenedioxyohenyl)-2-butanamine, lysergic acid diethylamide, and combinations thereof.

Chemical warfare agents and other toxins that can be analyzed include, but are not limited to amiton (VG), anthrax, arsine, cyanogen chloride, hydrogen chloride, chlorine, diphosgene, PFIB, phosgene, phosgene oxime, chloropicrin, ethyl N,N-dimethyl phosphoramicocyanidate (Tabun), isopropyl methyl phosphonofluoridate (Sarin), cyclosarin, pinacolyl methyl phosphonefluoridate (Soman), phosphonofluoridic acid, ethyl-, isopropyl ester (GE), phosphonothioic acid, ethyl-, S-(2-(diethylamino)ethyl) O-ethyl ester (VE), phosphonothioic acid, methyl-, S-(2-(diethylamino)ethyl) O-ethyl ester (VM), distilled mustard, ethyldichloroarsine, lewisite 1, lewisite 2, lewisite 3, methyldichloroarsine, mustard-lewisite mixture, mustard-T mixture, nitrogen mustard 1, nitrogen mustard 2, nitrogen mustard 3, phenyldichloroarsine, phosgene oxime, sesqui mustard, adamsite, aflatoxin, botulinus toxin, ricin, saxitoxin, trichothecene mycotoxin, methylphosphonothioic acid S-(2-(bis(1-methylethyl) amino)ethyl) O-ethyl ester (VX), agent VX, cyclohexyl methylphosphonofluoridate (GF), and combinations thereof.

Chemical compounds that can be analyzed include, but are not limited to hydrogen cyanide (HCN), phosgene, $SO_2$, $NH_3$, Etox, $HNO_3$, HCL, $CL_2$, HF, and combinations thereof.

FIGS. 1-4$b$ show an embodiment of a document sampler. A document sampler 10 can include a main unit 40, a front portion 50, and an insertion area 30.

Figure 1:
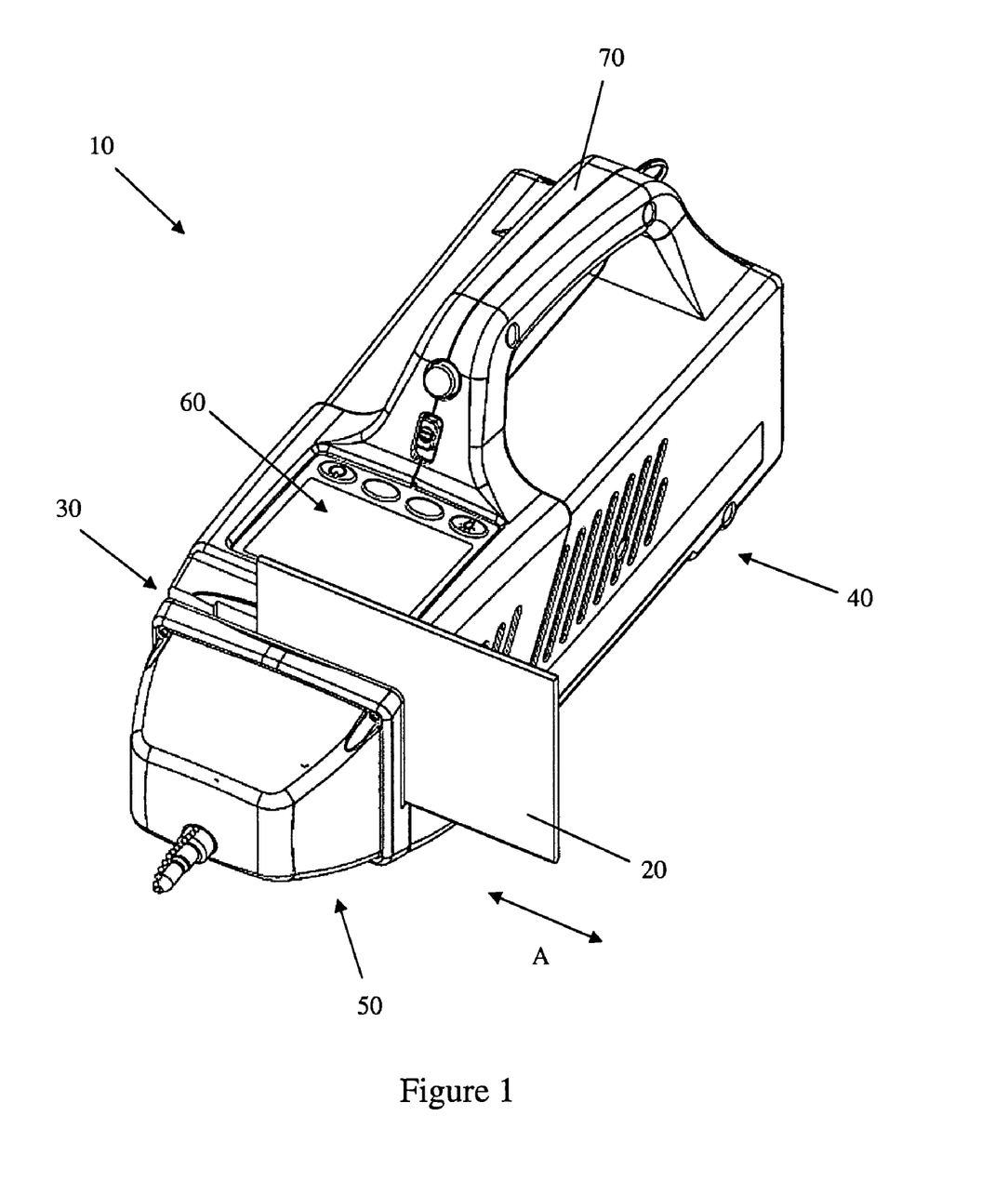
FIG. 1 shows a plan view of a document sampler.

FIG. 1 shows a plan view of a document sampler 10, according to an embodiment. A document sampler 10 can include a main unit 40 which houses an analytical device for the detection of an sample obtained from a document. An analytical device can be, for example, an IMS, an IMS-IMS, or a gas chromatographer-IMS. In one embodiment, the analytical device is an IM spectrometer. In another embodiment the analytical device is an IMS system having two IM spectrometers. According to a further embodiment, a main unit 40 can include a interface 60 for an operator and a handle 70 to facilitate use of a document sampler 10.

A document sampler 10 can include a front portion 50 and an insertion area 30. An insertion area 30 can be a location where a document can be inserted into a document sampler 10 so that a sample can be collected from the document for analysis. For example, an insertion area 30 can be arranged to permit a document to be inserted directly into a document sampler for sample collection. According to an embodiment, a main unit 40 and a front portion 50 can cooperate to form an insertion area 30 between the main unit 40 and the front portion 50. As shown in the example of FIG. 1, a document 20 can be inserted into a document sampler 10 by sliding the document 20 through an insertion area 30 in the direction indicated by arrow A. For example, a document 20 can be slid through an insertion area 30 so that the document passes completely through the insertion area 30 from one end of the insertion area 30 to the other end of the insertion area 30.

Figure 2:
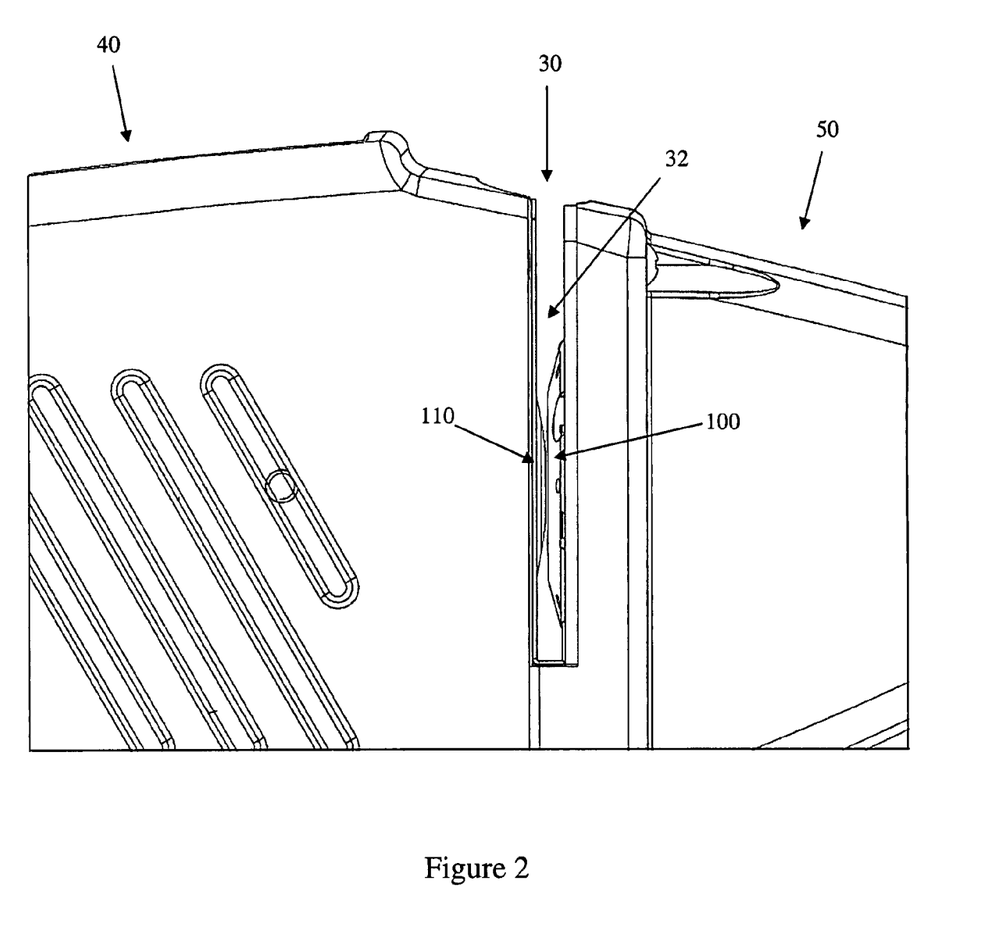
FIG. 2 is a side view of a document sampler.

FIG. 2 shows a side view of a document sampler, particularly an insertion area 30 of a document sampler. According to an embodiment, a front portion 50 can include a desorber area 100 and a main unit 40 can include an inlet 110, as will be described below. An insertion area 30 can form a slot 32 that a document is inserted into. For example, a document can be inserted into an insertion area 30 that is formed between a main unit 40 and a front portion 50 by sliding the document through a slot 32 so that a sample can be collected from the document for analysis.

According to an embodiment, a signal from a sensor can be used to indicate that a document has been inserted into the document sampler and that analysis should commence. According to another embodiment, a document sampler can include a sensor that detects when a document has been inserted in an insertion area. For example, a signal from such a sensor can be used to initiate sample collection or sample analysis once a document has passed through an insertion area. According to another embodiment, a document sampler can include a sensor that detects when a document has exited an insertion area. For example, a signal from such a sensor can be used to initiate sample collection or sample analysis once a document has passed through an insertion area. According to another embodiment, a document sampler can include a first sensor that detects when a document has been inserted in an insertion area and a second sensor that detects when the document has exited the insertion area. For example, a signal from the first sensor can be used to initiate sample collection once a document has been inserted into an insertion area and a signal from the second sensor can be used to initiate sample analysis once the document has exited the insertion area.

Figure 3A:
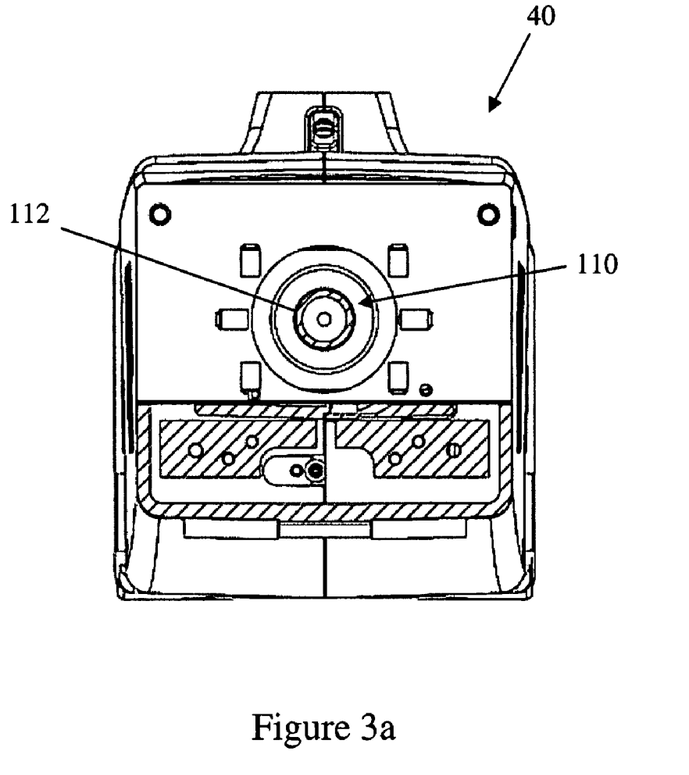
FIG. 3a is an end view of a main unit of a document sampler.
Figure 3B:
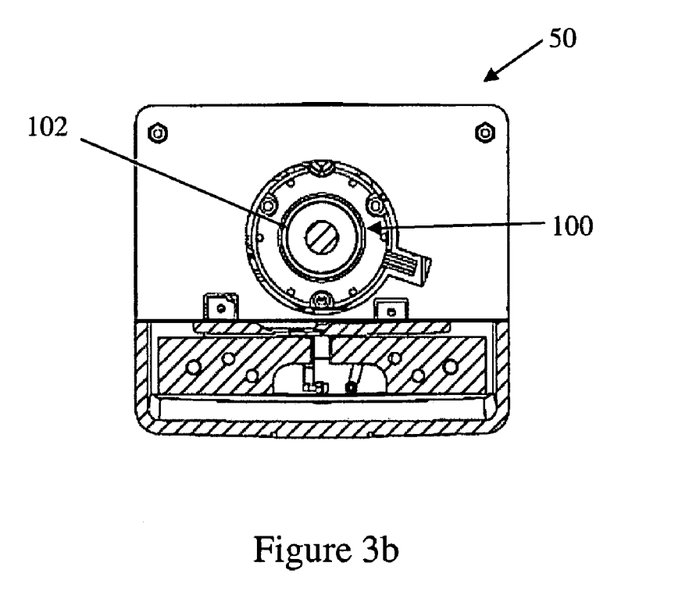
FIG. 3b is an end view of a front portion of a document sampler.

FIG. 3a shows an end view of a main unit 40 of a document sampler and FIG. 3b shows an end view of a front portion 50 of a document sampler. As shown in the example of FIG. 3b, a front portion 50 can include a desorber area 100 and a mesh 102 that is fixed to the front portion 50. Mesh 102 can be configured to cover a desorber area 100 so that the mesh 102 comes into contact with a document that is inserted into an insertion area 30 of a document sampler. According to such an arrangement, a sample can be collected from a document by mesh 102 when the mesh 102 comes into contact with a document that is inserted into an insertion area 30. For example, mesh 102 can be arranged to contact a document that is slid through an insertion area 30, such as a slot 32, causing the mesh 102 to contact the document along its length as the document is slid through the insertion area 30 while in contact with the mesh 102.

As shown in the example of FIG. 3a, a main unit 40 can include an inlet 110 and a mesh 112 that is fixed to the main unit 40. Mesh 112 can be configured to cover an inlet 110 so that the mesh 112 comes into contact with a document that is inserted into an insertion area 30 of a document sampler. According to such an arrangement, a sample can be collected from a document by a mesh 112 when the mesh 112 comes into contact with a document that is inserted into an insertion area 30. For example, mesh 112 can be arranged to contact a document that is slid through an insertion area 30, such as a slot 32, causing the mesh 112 to contact the document along its length as the document is slid through the insertion area 30 while in contact with the mesh 112.

An inlet 110 can be configured to receive samples that have been collected from a document by mesh 102, 112. An inlet 110 can receive samples by an air flow, or other non-interfering gas, such as, for example, a forced air flow through an insertion area and into an inlet 110, a suction air flow that draws samples into an inlet 110, or a combination of forced air flow and suction air flow. A document sampler can be arranged so that such airflows pass through mesh 102, mesh 112, or both mesh 102 and mesh 112. An inlet 110 can be configured to provide samples to an analytical device, such as an IMS, housed within a main unit 40 so that the samples can be analyzed.

A desorber area 100 can include desorber to facilitate acquisition of a sample from mesh 102, 112. A desorber can include a desorber heater to raise the temperature of a sample. A desorber heater, or other thermal process such as infrared or laser heating, can be configured to operate simultaneously with an air flow for introducing a sample into an inlet 110. A desorber heater can be configured to quickly attain all operating temperature for desorption of samples that have been collected upon mesh 102, 112. For example, a desorber heater can be configured to reach a temperature of up to approximately 200° C. for desorption of samples collected upon mesh 102, 112. A desorber heater can also be configured to quickly cool once samples have been acquired from mesh 102, 112 so that samples can be collected from a subsequent document without damage to the document. For example, a desorber heater can be configured to cool to approximately 30-70° C., or preferably approximately 40-65° C., or more preferably approximately 50-60° C. An air flow used for sample introduction into an inlet 110 can be used to facilitate cooling of a desorber heater and increased flow rates of an air flow can be used to enhance a cooling effect of the forced air.

Mesh 102, 112 can be configured to contact a substantial area of a document that is inserted into a document sampler. According to an embodiment, mesh 102, 112 can be configured to contact a document along a vertical dimension of the mesh. Such a vertical dimension can be, for example, approximately 1-6 cm, or more preferably approximately 1-4 cm, or more preferably approximately 2-3 cm. Therefore, mesh 102, 112 can be configured to contact a document across an entire length of the document it is slid past mesh 102, 112 and within a vertical distance that corresponds to a height of mesh 102, 112. Furthermore, by arranging mesh 102 and mesh 112 on opposite sides of an insertion area 30, both sides of a document can be contacted by mesh 102, 112 for sample collection and more surface area of a document can be contacted and analyzed. Mesh 102, 112 can be configured to have a curved outer shape.

Mesh 102, 112 can be made of metal, such as, for example, steel, stainless steel, and other materials known in the art. Mesh 102, 112 can be made of a material that is resistant to wear, resistant to operating temperatures of a desorber heater, and does not pose a contamination hazard for analysis of samples.

Figure 4A:
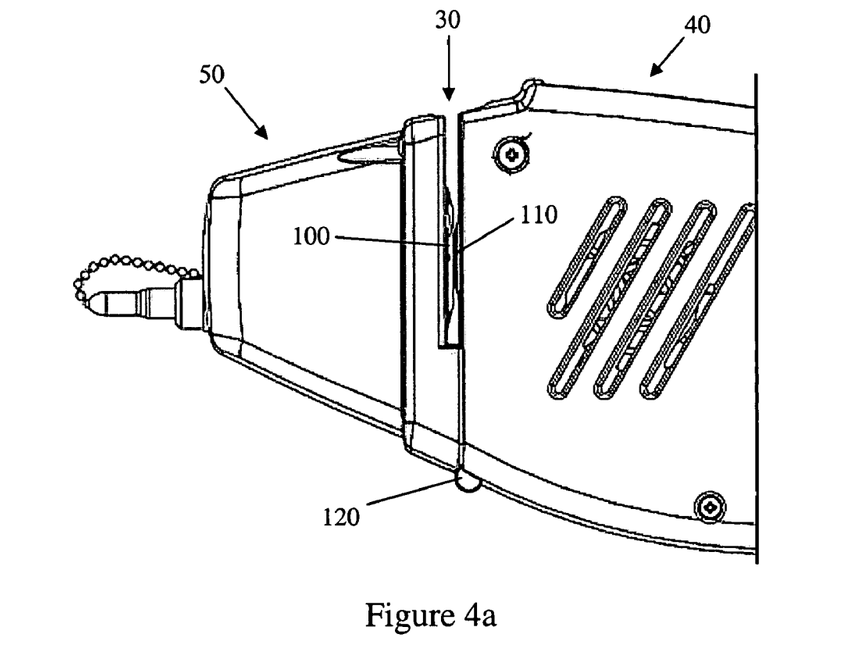
FIG. 4a is a side view of an insertion area when a front portion of a document sampler is in a closed state.
Figure 4B:
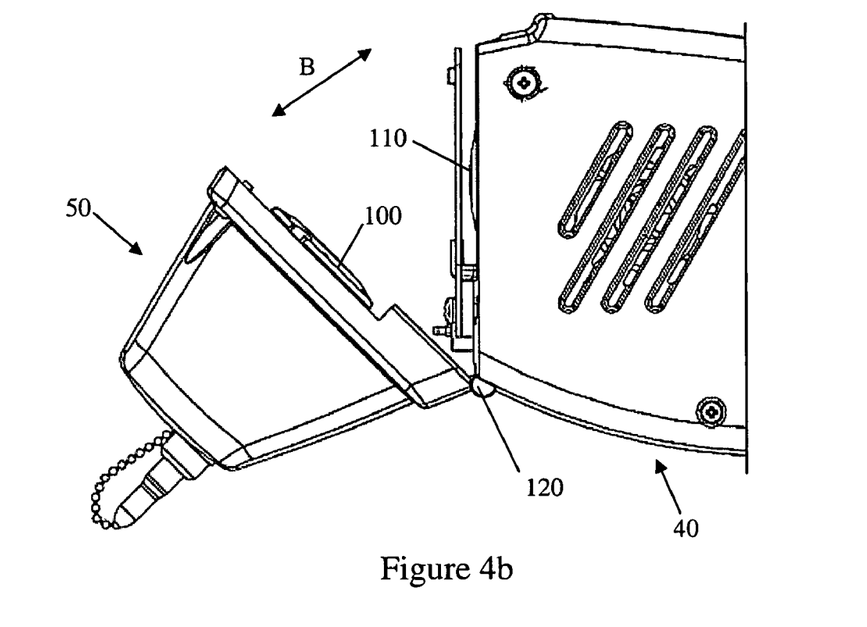
FIG. 4b is a side view of an insertion area when a front portion of a document sampler is in an open state.

FIG. 4a is a side view of an insertion area when a front portion of a document sampler is in a closed state. FIG. 4b is a side view of an insertion area when a front portion of a document sampler is in an open state. As shown in the examples of FIGS. 4a and 4b, a document sampler can include a pivot axis 120 that permits a front portion 50 to pivot and move in the direction indicated by arrow B. Such a configuration permits easy access to an insertion area 30 and mesh 102, 112 at desorption area 100 and inlet 110.

A method of sampling a document by using a document sampler will now be described, according to an embodiment and reference to the examples shown in FIGS. 1-4b. A document 20 that is targeted for analysis is inserted into an insertion area 30 of a document sampler 10. A document sampler 10 can include a main unit 40 and a front portion 50. An insertion area 30 can be a slot 32 and can be formed between a main unit 40 and a front portion 50 of a document sampler 10. When the document 20 is inserted into an insertion area 30, the document 20 can come into contact with mesh 102 and/or mesh 112 so that mesh 102 and/or mesh 112 can collect a sample from the document. A sample is then acquired from mesh 102 and/or mesh 112 by application of heat from a desorption heater within a desorption area 100 and/or an air flow that passes through mesh 102 and/or mesh 112 to introduce the sample into an inlet 110 for analysis by an analytical device housing within main unit 40. After sample acquisition is complete, decontamination of inlet 110, mesh 102, and mesh 112 can be performed via air flow to flush residual sample materials. If a desorber heater has been used during sample acquisition, the desorber heater is cooled down to a sample collection temperature and the above steps can be repeated for sample collection from another document. According to an embodiment, a document sampler can be used to analyze approximately 2 documents per minute, or preferably up to 10 documents per minute.

FIGS. 5-10 show an embodiment of a document sampler 200 that includes a sampling module 210 and an IMS device 220.

Figure 5:
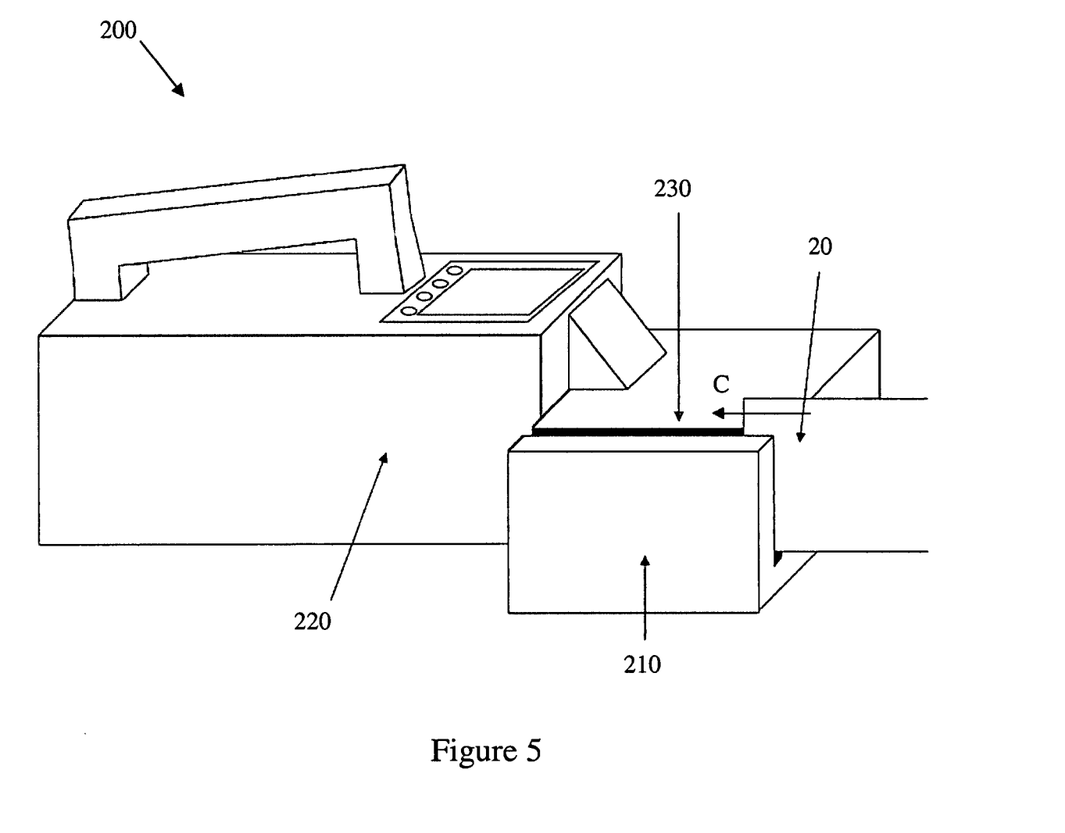
FIG. 5 is a plan view of a document sampler.

FIG. 5 shows a plan view of a document sampler 200 that includes an analytical device 220 and a sampling module 210 that a document 20 can be inserted into. A sampling module 210 can include an insertion area 230 that a document 20 can be inserted into for analysis. According to an embodiment, a document 20 can be inserted into an insertion area 230 of a sampling module 210 by sliding the document 20 in a direction indicated by arrow C. For example, a document 20 can be slid in the direction indicated by arrow C so that the document 20 passes from one end of the insertion area 230 to the other end of the insertion area 230.

An analytical device 220 can be an IMS device. For example, an analytical device 220 can be an IONSCAN® 400B, IONSCAN® 500DT, Sabre 4000, or other IMS device known in the art. Furthermore, the analytical device 220 can be any embodiment of document sampler 10 described above, wherein a front portion 50 of the document sampler 10 has been removed so that an inlet 110 of a main unit 40 can be engaged with a sampling module 210 of a document sampler 200.

Figure 6:
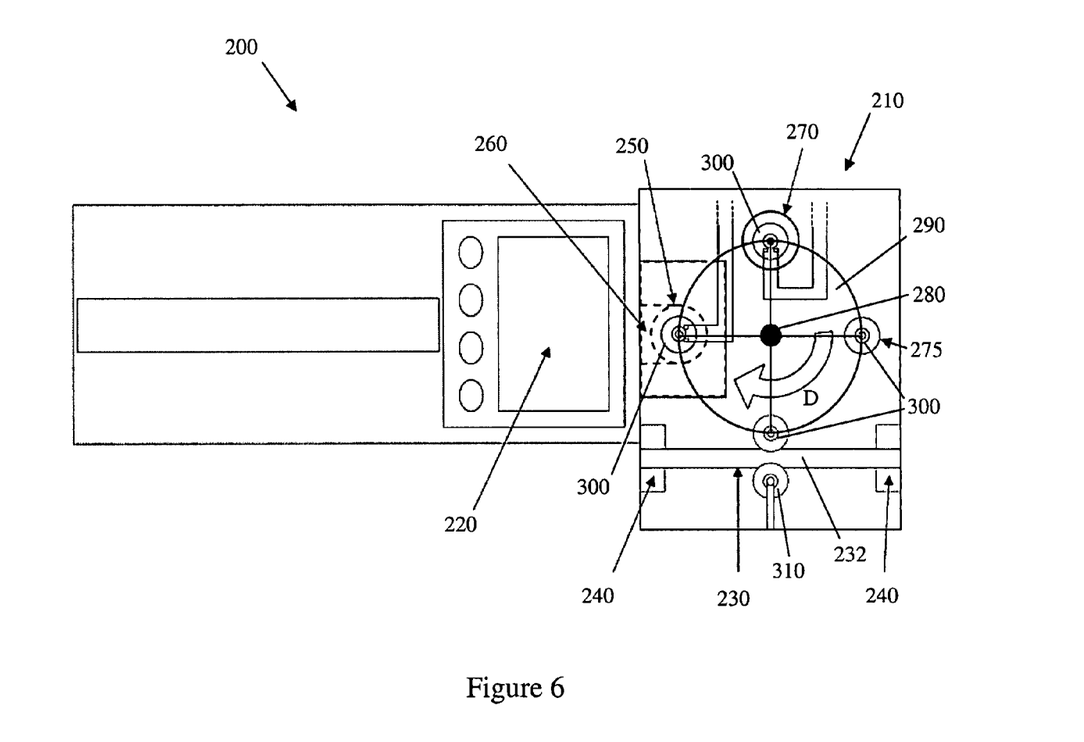
FIG. 6 is a top view of a document sampler.

FIG. 6 shows a top view of a document sampler 200 in which internal components of a sampling module 210 can be viewed. According to an embodiment, a sampling module 210 can include an insertion area 230 that a document 20 can be inserted into for sample collection. As shown in the example of FIG. 6, an insertion area 230 can include a slot 232 formed within a sampling module 210 so that a document 20 can be inserted into the slot 232 for sample collection. For example, a document 20 can be slid through the slot 232 as indicated by arrow E in FIGS. 7 and 8.

A sampling module 210 can include sensors 240 that detect when a document 20 has been inserted into insertion area 230. For example, sensors 240 can be arranged to produce a signal that a document 20 has been slid through slot 232. A signal from such sensors 240 can be used to indicate that a document 20 has been inserted into the insertion area 230, or that a document 20 has been slid through slot 232, and that analysis should commence. Although the example of FIG. 6 shows a document sampler 200 with two sensors 240, other sensor arrangements can be used. For example, a single sensor 240 can be positioned at the exit or entrance of the insertion area 230.

A sampling module 210 can include a plurality of rollers 300 that contact a large area of a document 20. As will be described below, rollers 300 are cylindrical and are configured to contact a document 20 that is inserted into an insertion area 230 of a sampling module 210. For example, a roller 300 can be configured to roll as a document 20 contacts the roller 300 and moves past the roller 300 in the insertion area 230, causing the roller 300 to roll over the document 20 as the document 20 is moved past the roller 300 in the insertion area 230. According to an embodiment, rollers 300 are configured to contact a substantial surface area of a document 20.

According to an embodiment, a pressure roller 310 can be positioned within an insertion area 230 to bias a document 20 towards a roller 300 within the insertion area. For example, a pressure roller 310 can be spring loaded so that the pressure roller 310 biases a document 20 towards a roller within an insertion area.

Figure 9:
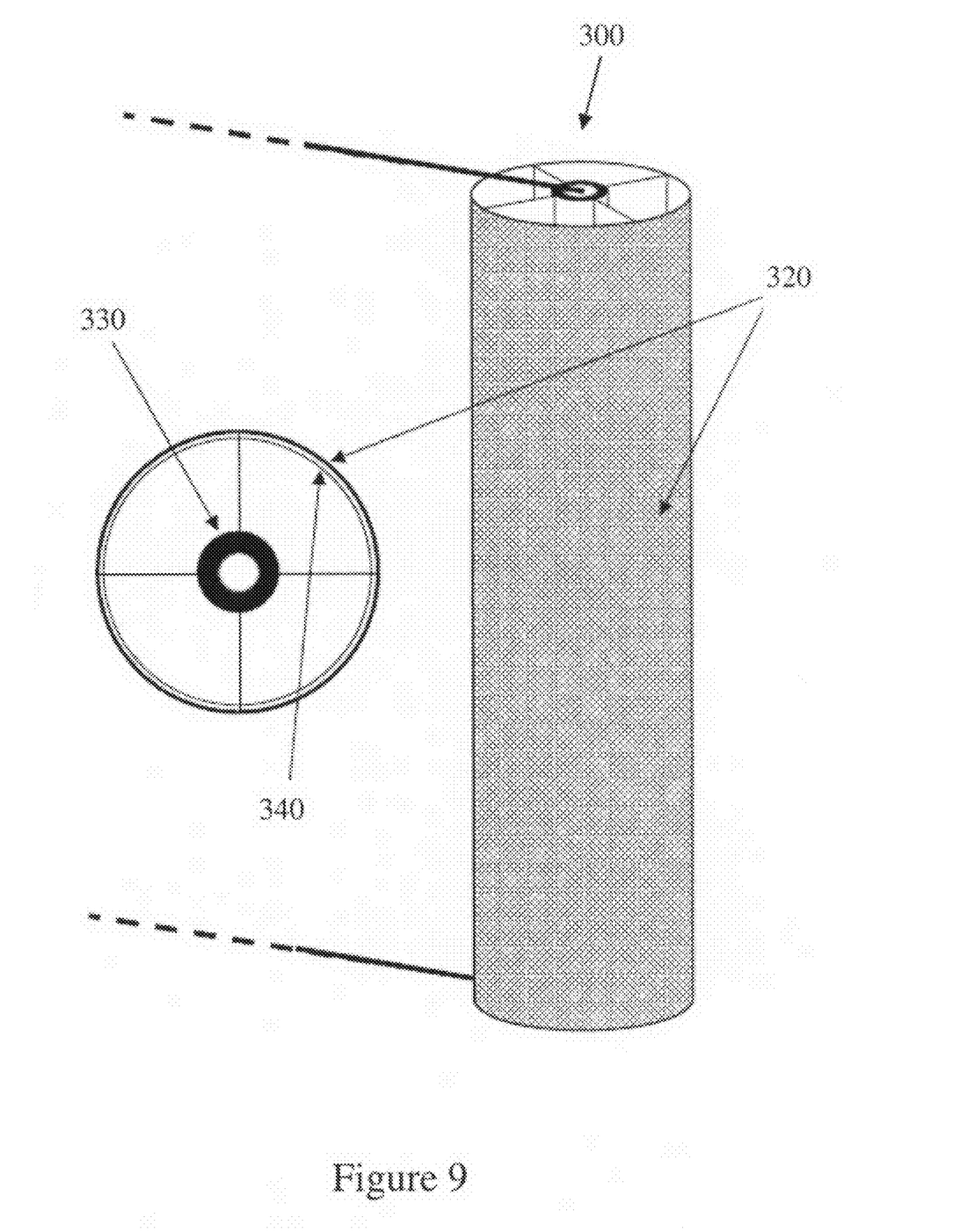
FIG. 9 is a top view and a plan view of a roller.
Figure 10:
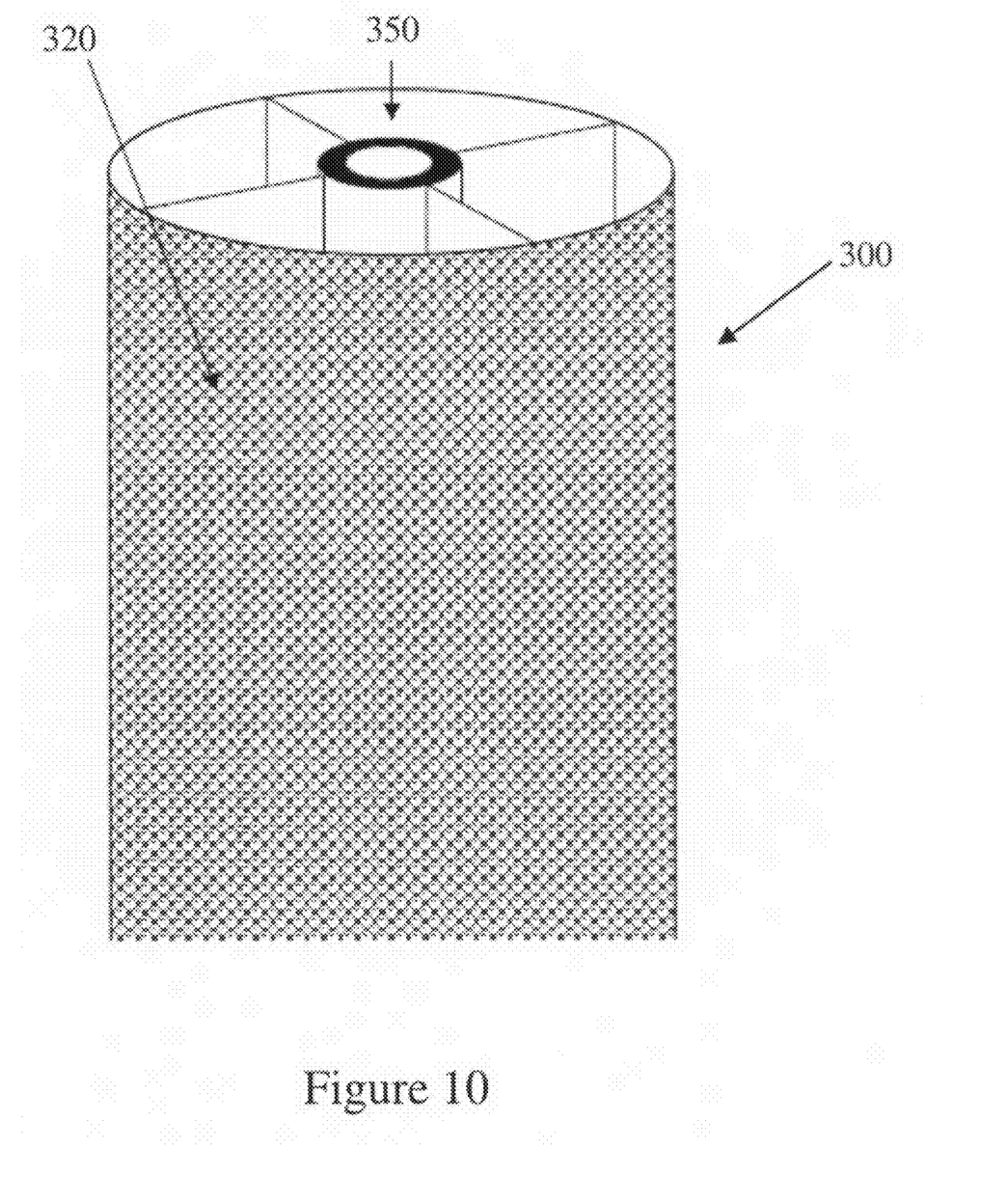
FIG. 10 is an enlarged plan view of a roller.

Rollers 300 can be made of a mesh material 320, as shown in the examples of FIGS. 9 and 10. For example, rollers can be made of a metal mesh. Metal mesh can be made of metals, such as, for example, steel, stainless steel, and other materials known in the art. Rollers 300 can be made of a material that is resistant to wear, resistant to operating temperatures of a desorber heater, and does not pose a contamination hazard for analysis of samples. As shown in the example of FIG. 9, rollers 300 can include a heater contact 330 and a heater lining 340 arranged underneath an outer surface of the rollers 300. A heater contact 330 and heater lining 340 can be used to facilitate heating of rollers 300, as will be described below. As shown in the example of FIG. 10, a roller 300 can include an air flow opening 350 to facilitate the passage of an air flow through the roller 300, such as during acquisition of a sample from the roller 300 at analysis stage 250 and/or cleaning of the roller 300 at cleaning stage 270.

As shown in the example of FIG. 6, a sampling module 210 can include a plurality of rollers 300 that are arranged so that one roller 300 is configured to contact a document in an insertion area 230 and collect a sample, a roller 300 is arranged at an analysis stage 250 at an inlet 260 to an analytical device 220, a roller 300 is arranged at a cleaning stage 270, and a roller 300 is in a ready position 275 for deployment to the insertion area 230. According to such an arrangement, a roller 300 can be used to contact a document 20 in an insertion area 230 while another roller 300 that has previously collected a sample from a document is being analyzed at an inlet 260 and another roller 300 is undergoing a cleaning treatment in a cleaning stage 270.

Figure 7:
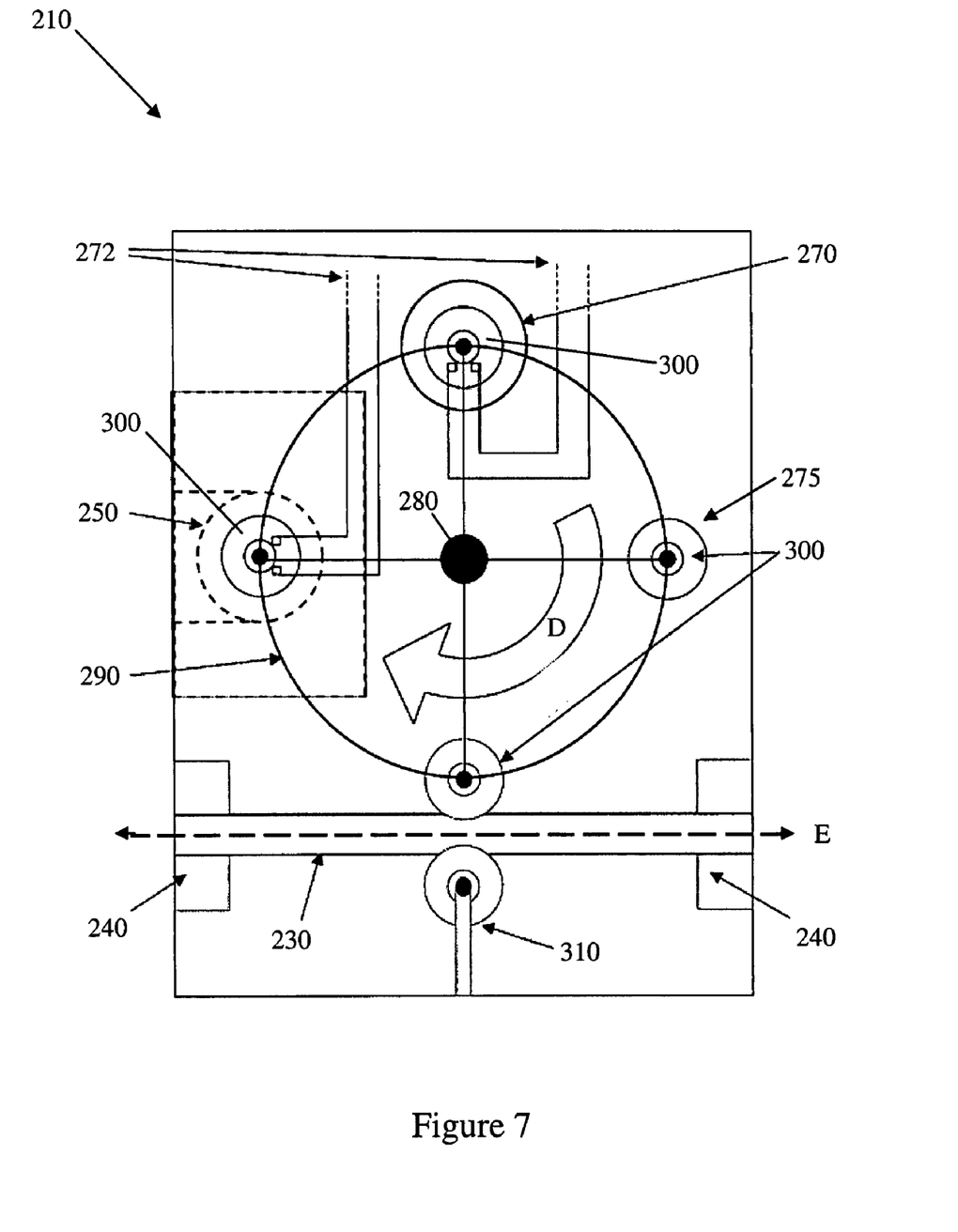
FIG. 7 is a top view of a sampling module.

According to an embodiment, a sampling module 210 can include a turntable or carousel 290 that supports a plurality of rollers 300 and is configured to rotate about a central axis. For example, a carousel 290 can include a central shaft 280 that the carousel 290 is configured to rotate about. As shown in the examples of FIGS. 6 and 7, a carousel 290 can be configured to rotate in a direction indicated by arrow D so that rollers 300 revolve with the carousel 290 from point to point around the circumference of carousel 290. A carousel 290 can be configured to rotate in a clockwise or counterclockwise direction. According to an embodiment, a carousel 290 can be configured to revolve a roller 300 from an insertion area 230 to an analysis stage 250 after the roller 300 has collected a sample from a document, to revolve a roller 300 from an analysis stage 250 to a cleaning stage 270 after a sample has been acquired from the roller 300, to revolve a roller 300 from the cleaning stage 270 to a ready position 275 after cleaning is complete, and to revolve a roller from a ready position 275 to the insertion area 230. According to an embodiment, a carousel 230 can be configured to revolve a plurality of rollers 300 from multiple positions (such as an insertion area 230, an analysis stage 250, a cleaning stage 270, and a ready position 275) at once. According to an embodiment, a signal from one or more sensors 240 can be used to activate the carousel 290 and move rollers 300 to a next position in the direction of arrow D.

FIG. 7 shows an enlarged top view of a sampling module 210. As shown in the example of FIG. 7, a sampling module 210 can include an analysis stage 250 for acquiring a sample from a roller 300. Samples acquired from rollers 300 are received by an inlet 260 for analysis by an analytical device 200.

Figure 8:
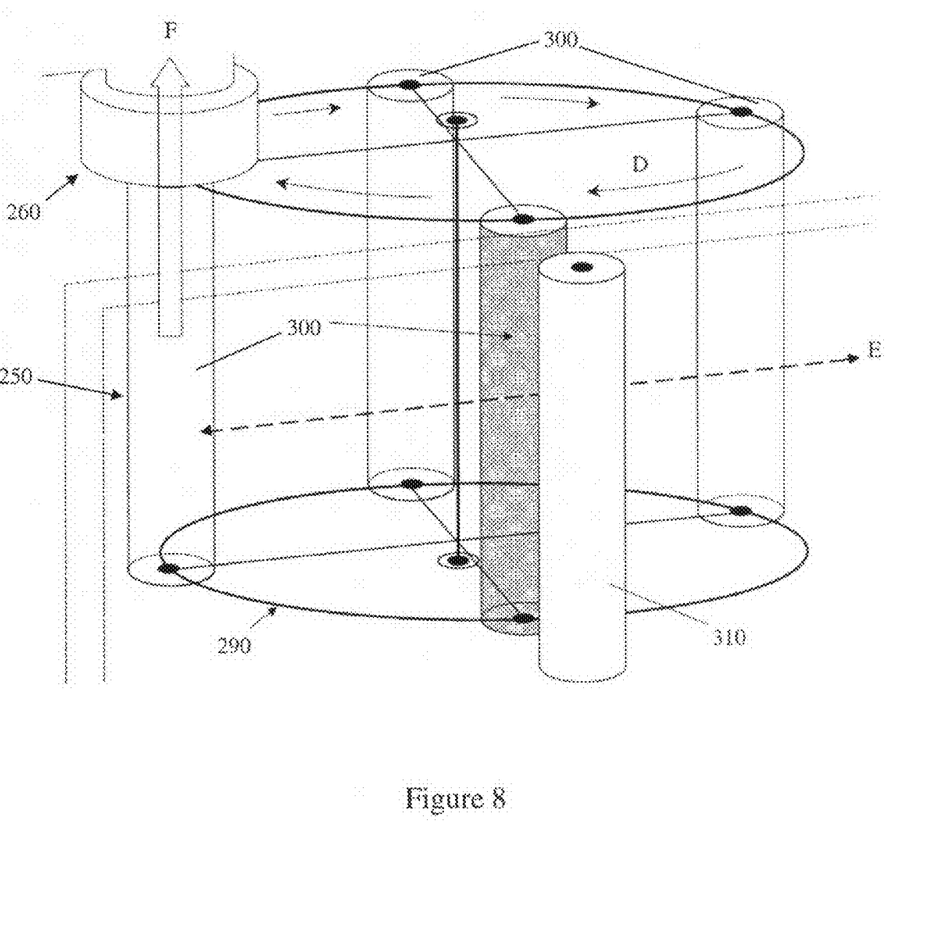
FIG. 8 is a plan view of a carousel of a sampling module.

According to an embodiment, an inlet 260 of an analytical device 220 can be configured to receive samples that have been collected from a document by roller 300 at an analysis stage 250. As shown in the example of FIG. 8, an analytical stage 250 can be configured so that a roller 300 positioned within the analytical stage 250 is positioned below an inlet 260. An analytical stage 250 can be configured so that once a roller 300 is positioned within the analytical stage 250 the roller 300 is fully enclosed. Enclosure of a roller 300 in an analytical stage 250 can be performed to facilitate acquisition of samples from the roller 300. According to an embodiment, a document sampler 200 can be configured so that sampler acquisition automatically commences once a roller 300 has been positioned at an analytical stage 250.

An inlet 260 can receive samples by an air flow in analytical stage 250. For example, an air flow can be directed through a roller 300 in a direction indicated by arrow F in FIG. 8. According to an embodiment, a forced air flow can be directed through a roller 300 and into an inlet 260, a suction air flow can be directed through a roller 300 to draw samples into an inlet 260, or a combination of forced air flow and suction air flow can be used.

An analytical stage 250 can include a desorber heater to facilitate acquisition of a sample from rollers 300. According to an embodiment, a desorber heater can provide energy through energy supply 272 to a heater contact 330 and a heater lining 340 of a roller 300 in order to heat a roller 300. A desorber heater can be configured to operate simultaneously with an air flow for introduction of a sample into an inlet 260. A desorber heater can be configured to quickly attain an operating temperature for desorption of samples that have been collected upon rollers 300. For example, a desorber heater can be configured to reach a temperature of up to approximately 200° C. for desorption of samples collected upon rollers 300.

According to an embodiment, a sampling module 210 can include a cleaning stage 270. A cleaning stage 270 can be an area that fully encloses a roller 300 that is positioned with the cleaning stage 270. A cleaning stage 270 can be configured to clean a roller 300 by heating the roller 300 to a cleaning temperature. For example, a cleaning stage 270 can provide energy through energy supply 272 to a heater contact 330 and a heater lining 340 of a roller 300 in order to heat a roller 300 to a cleaning temperature. A cleaning operation can be performed at a cleaning stage 270 to remove contaminates from a roller 300 and prepare the roller 300 for sample collection in insertion area 230. According to an embodiment, a document sampler 200 can be configured so that cleaning automatically commences once a roller 300 has been positioned at a cleaning stage 270.

It should be understood, however, that the invention, as claimed, is not limited to the specific embodiments described in these examples. It will be apparent to those skilled in the art that various modifications and variations can be made to the embodiments of the claimed invention without departing from the spirit or scope of the claimed invention. Thus, it is intended that the claimed invention covers other modifications and variations within the scope of the appended claims and their equivalents.

What is claimed is:

1. A document sampler, comprising:
   an analytical device;
   an insertion area formed by the document sampler, wherein the insertion area is configured so that a document can be inserted into the document sampler; and
   at least one mesh located in the insertion area, wherein the mesh is configured to contact the document to collect across a surface of the mesh a sample.

2. The document sampler of claim 1, wherein the insertion area is a slot.

3. The document sampler of claim 1, wherein the at least one mesh comprises a first mesh and a second mesh, wherein the first mesh is positioned on a first side of the insertion area to contact a first side of the document, wherein the second mesh is positioned on a second side of the insertion area to contact a second side of the document.

4. The document sampler of claim 1, wherein the mesh comprises metal mesh.

5. The document sampler of claim 1, wherein the analytical device is an IMS device.

6. The document sampler of claim 1, further comprising a desorber.

7. The document sampler of claim 1, wherein the document sampler is configured to provide an air flow in the insertion area.

8. The document sampler of claim 1, further comprising a sensor that is configured to detect insertion of the document into the insertion area.

9. The document sampler of claim 8, wherein the document sampler is configured to automatically initiate sample collection from the document when the sensor produces a signal.

10. The document sampler of claim 8, further comprising a second sensor that is configured to detect an exit of the document from the insertion area.

11. The document sampler of claim 10, wherein the document sampler is configured to automatically initiate analysis of a sample collected from the document when the second sensor produces a signal.

12. The document sampler of claim 1, further comprising at least one roller located in the insertion area, wherein the roller is configured to contact the document.

13. The document sampler of claim 12, further comprising a carousel that is configured to support the at least one roller, wherein the carousel is configured to rotate about a central axis.

14. The document sampler of claim 13, wherein each roller comprises at least one mesh.

15. The document sampler of claim 12, further comprising a pressure roller located in the insertion area.

16. The document sampler of claim 12, further comprising a cleaning stage.

17. A method of acquiring and analyzing samples from documents, comprising:
    inserting a document into an insertion area of a document sampler;
    contacting the document with a mesh to collect a sample across the surface of the mesh; and
    providing the sample to an analytical device for analysis.

18. The method of claim 17, further comprising decontamination after providing the sample to the analytical device.

19. The method of claim 17, wherein the document sampler comprises at least one roller located in the insertion area, wherein the roller comprises the mesh.

* * * * *